United States Patent [19]
Conrad et al.

[11] Patent Number: 5,827,643
[45] Date of Patent: Oct. 27, 1998

[54] METHOD OF INCREASING VIABILITY OF STORED ERYTHROCYTES BY ADDITION OF LIPOIC, DIHYDROLIPOIC, 6,8-BISNORTETRALIPOIC, OR TETRANORLIPOIC ACID

[75] Inventors: Frank Conrad, Frankfurt; Hermann-August Henrich, Wurzburg; Wolfgang Geise, Dipbach; Heinz Ulrich, Niedernberg, all of Germany

[73] Assignee: ASTA Medica Aktiengesellschaft, Dresden, Germany

[21] Appl. No.: 554,421

[22] Filed: Nov. 8, 1995

[30] Foreign Application Priority Data

Nov. 8, 1994 [DE] Germany ............ 44 39 480.2

[51] Int. Cl.$^6$ .................................................. A01N 1/02
[52] U.S. Cl. ........................................ 435/2; 604/4
[58] Field of Search ................................. 435/2; 604/4

[56] References Cited

U.S. PATENT DOCUMENTS 4,229,435  10/1980  Blombäck et al. ................. 424/101

OTHER PUBLICATIONS

Rozanov A et al., Ukr. Biokhim. Zh. 49:45–8 (1977).

Constantinescu A et al, J. Biol. Chem. 268:10906–13 (1993).

Mueller U et al, Evol. Antioxid. Mod. Med. (1994), 57–64 Editors: Schmidt, Diplock and Ulrich.

Hofmann M et al, Arch Biochem Biophys 324:85–92 (1995).

*Primary Examiner*—Sandra E. Saucier
*Attorney, Agent, or Firm*—Cushman Darby & Cushman IP Group of Pillsbury Madison & Sutro LLP

[57] ABSTRACT

A method of improving the properties of liquid stored or cryogenically stored erythrocytes using D,L-α-lipoic acid and/or enantiomers or derivatives thereof. Treatment with these substances results in improved oxygen release capacity (2,3-DPG), viscoelasticity and erythrocyte aggregability, and increased resistance to membrane peroxidation during storage and damage by the freeze/thaw process.

6 Claims, 1 Drawing Sheet

FIG. I
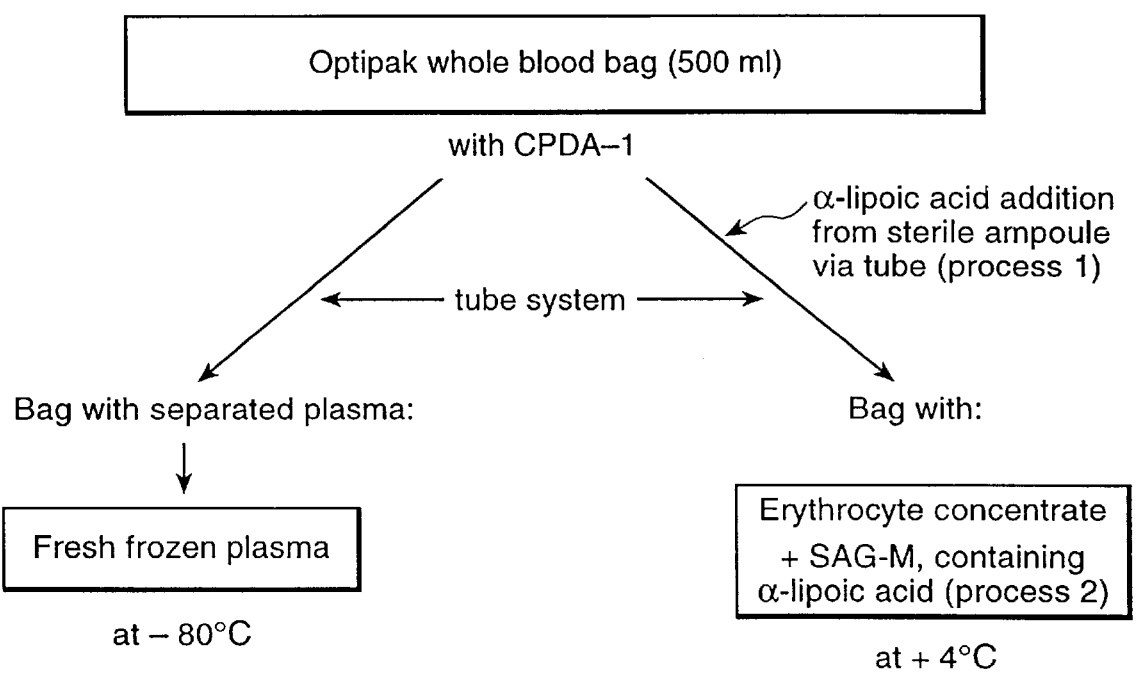

METHOD OF INCREASING VIABILITY OF STORED ERYTHROCYTES BY ADDITION OF LIPOIC, DIHYDROLIPOIC, 6,8-BISNORTETRALIPOIC, OR TETRANORLIPOIC ACID

BACKGROUND OF THE INVENTION

1. Field of the Invention

This invention relates to improved methods for storing blood and blood constituent products containing cells by addition of D,L-α-lipoic acid and/or enantiomers or derivatives thereof prior to storage.

2. Background Information

α-Lipoic acid is described chemically as 1,2-dithiolane-3-pentanoic acid, 5-(1,2-dithiolane-3-yl)valeric acid, 5-3-(1, 2-dithioanyl)pentanoic acid. α-Lipoic acid has a chiral C atom and occurs in two enantiomeric forms and is found physiologically in plants, bacteria and in mammals. It has the function of a coenzyme in mitochondrial multi-enzyme complexes, such as, for example, that of pyruvate dehydrogenase, α-ketoglutarate dehydrogenase and the dehydrogenases for branched amino acids. Through metabolic processes, α-lipoic acid may be converted from the oxidised form (disulphide bridge) into the reduced dihydro form with two free SH groups. Both forms have a pronounced antioxidative effect (for example Kuklinski et al., 1991; Packer, 1993). The dihydrolipoic acid/α-lipoic acid redox pair moreover has metal-chelating properties. The influence of α-lipoic acid on glucose transport has also recently been investigated (Bashan et al., 1993). In the Federal Republic of Germany, α-lipoic acid has been used since 1966 as a pharmaceutical for the treatment of liver conditions, in cases of poisoning by mushrooms, and in peripheral polyneuropathy.

Stored blood for clinical use is produced in accordance with BGA guidelines (see BGA notice, Bundgesgesundheitsblatt 2/92, Guidelines on Blood Grouping and Blood Transfusion), or the American guidelines (see Standards for Blood Banks and Transfusion Services, 14th edition 1991, Standards Committee, American Association of Blood Banks, Virginia).

The various types of stored blood are described as follows, in accordance with guidelines arising from various consensus meetings (see Arzneimittelbrief, 1994):

1. Stored blood and blood constituent products containing cells, such as: stored blood, stored fresh blood, erythrocyte concentrates, washed erythrocyte concentrates, low-leucocyte erythrocyte concentrates, leucocyte-free erythrocyte concentrates, deep frozen stored erythrocyte concentrates, high-thrombocyte plasma, thrombocyte concentrates, leucocyte concentrates;

2. Plasma and plasma fractions: not relevant in this case.

Erythrocyte concentrates are stored blood from which the plasma has largely been removed. They are now the standard preparation for erythrocyte replacement, for example in the event of acute blood loss and chronic anaemia (Welch, G., et al., 1992). Washed erythrocyte concentrates have a low leucocyte content ($<1.2\times10^9$ depending upon the product) and are used in patients with IgA-deficiency syndrome and IgA antibodies, in autoimmune haemolytic anaemia with complement involvement and in paroxysmal nocturnal haemoglobinuria (more rarely). Cryogenically stored blood is deemed to contain no leucocytes after thawing and removal of antifreeze, and relates to the same indications as erythrocyte concentrates.

Optimum storage conditions are governed by the above-stated guidelines (Stangel W., 1988), wherein the necessary minimum requirements are defined in these documents. Storage periods are stated by the manufacturer in the expiration date as a function of the production process. The quality of stored blood containing erythrocytes is temperature-dependent; it should be cooled within 30–60 minutes and, if cooling is delayed by six hours, it exhibits a loss of 2,3-Diphosphoglycerate (2,3-DPG). 2,3-DPG is present in erythrocytes as a glycolysis intermediate and has an important function in regulating oxygen transport. Deoxyhaemoglobin (without oxygen) binds 2,3-DPG, and thereby sharply reduces oxygen affinity. Under the more alkaline conditions in the lungs, 2,3-DPG dissociates from the haemoglobin, and thereby increases its affinity for loading with $O_2$. 2,3-DPG content falls in older stored blood, and deoxyhaemoglobin consequently contains less of it and binds oxygen much more strongly. It was first established as long ago as 1954 that the oxygen dissociation curve is displaced to the left after only one week, so that these erythrocytes no longer release the same quantity of oxygen in the tissues as freshly drawn erythrocytes. After transfusion, this displacement to the left normalises over the course of 24–48 hours. This displacement to the left was interpreted to be a consequence of the failure of glycide metabolism, which is expressed as a reduction in the quantity of reduced glutathione. Reduced glutathione is produced by glutathione reductase and NADPH. It subsequently became evident that the displacement to the left described above is accompanied by the loss of 2,3-DPG during storage. CPD blood exhibits a less marked displacement of the dissociation curve to the left than ACD blood; this is associated with a higher 2-DPG level.

The ATP content of the erythrocytes falls during storage and, in parallel, lipid losses from the cell membranes, spherocytosis and an increase in cell rigidity all occur. Normal viability of erythrocytes after transfer into the receiving organism is the most important parameter by which the success of blood storage may be measured. The percentage of erythrocytes surviving for longer than 24 hours in the recipient's circulation is now stated as a measure of the effectiveness of erythrocyte preservation. Currently applicable regulations concerning preservation solutions and storage conditions require that at least 70% of the transfused cells must be detectable in the recipient's circulation after 24 hours. A reduced tendency to erythrocyte aggregation (rouleau formation) may also be detected in vitro as a function of storage time. While storage time has no influence upon the blood group features ABO and Rh, a loss in reactivity of the Lewis and P blood group features has been described with increasing age of the stored blood. A major precondition for blood storage is the prevention of clotting (Stangel, W., 1988). This is currently achieved by a mixture of sodium citrate and citric acid. Investigations showed that at a temperature of 4° C. and at a pH of between 6.8 and 7.2, the ATP level remains stable. As a consequence of the introduction of a glucose/citrate solution acidified with citric acid, the expiration date of stored blood could be extended to 21 days. In order to stabilise the pH value, preservation solutions (stabilisers) are used which have a pH of 7.0–7.1 for ACD stored blood and of 7.1–7.2 for CPD and CPDA-1 stored blood. Clinically, CPDA1 and SAG-M are currently used as stabiliser solutions and were also used in the patent applicant's investigations.

Other stabilisers solutions are known which differ from the above-stated solutions by having different concentrations of the same constituents or by having slightly changed compositions (see table 1 from: Meryman et al., 1990):

Compositions of red cell suspending solutions, mM.

| | CPDA-1 | ADSOL | Nutricell | ARC6 | ARC9C | ARC8 |
|---|---|---|---|---|---|---|
| NaCl | | 154.0 | 70.1 | | | |
| Adenine | 2.0 | 2.0 | 2.2 | 2.0 | 2.0 | 2.0 |
| Glucose | 161.0 | 11.0 | 55.0 | 110.0 | 177.0 | 138.0 |
| Mannitol | | 41.2 | | | | |
| Na-citrate | 89.6 | | 20.0 | 17.9 | 27.2 | 33.3 |
| Citric acid | 15.6 | | 2.0 | | | |
| $NaH_2PO_4$ | 16.1 | | 20.0 | 14.7 | | 3.26 |
| $Na_2HPO_4$ | | | | 25.8 | 20.0 | 11.6 |
| $NH_4Cl$ | | | | 50.0 | | |
| pH | 5.7 | 5.5 | 5.8 | 7.1 | 7.5 | 7.4 |
| Osmolality | 323 | 342 | 244 | 199 | 121 | 126 |

This table summarises the composition of solutions referred to in the text. Osmolality is presented in milliosmoles and refers only to the non-penetrating constituents, glucose being assumed to penetrate the red cell [12].

In addition to the CPDA-1 solution, stabiliser solution SAG-M is used in connection with the present invention: mg/100 ml distilled water. See also FIG. 1, process for the production of the erythrocyte concentrates used in this case using stabilisers CPDA-1 and SAG-M:

| | |
|---|---|
| Initial pH value for stored blood | 7.42 |
| NaCl | 877 |
| Glucose anhydride | 819 |
| Adenine | 16.9 |
| Mannitol | 525 |

A possible storage life of 35 days is stated for erythrocyte concentrates treated in this manner. The American Association of Blood Banks requires a haematocrit of below 80% for erythrocyte concentrates with this storage life (Stangel, W., 1988).

In the cryogenic process, erythrocyte concentrates are produced as described above and then combined with cryoprotective substances (glycerol for clinical use), deep frozen at $-196°$ C. and then stored at $-80°$ C. (Sputtek & Körber in: Fuller, B. J. and Grout B. W. W., 1991). A novel development which is currently undergoing tests is the use of hydroxyethyl starch as a cryoprotectant (storage in gas phase nitrogen at $-120°$ to $-140°$ C. (Langer et al., 1993 and Sputtek et al., 1992).

Human donated blood obtained using standardised methods is separated using automated processes into the 2 components "erythrocyte concentrate ($4°$ C.)" and "fresh frozen plasma". The Optipress System used for this purpose separates thrombocytes and leucocytes.

The provision of stocks of stored blood in order to ensure an adequate supply for operations or emergencies is associated with old, although still current, problems which have hitherto not been satisfactorily solved. In addition to the long term stability or functionality of stored erythrocytes, functionality after transfusion is very important to the hypoxic and ischaemic recipient organism. Preservation of erythrocytes also brings about peroxidation of membrane lipids, and structural or functional proteins, which results in dysfunction proceeding as far as haemolysis.

Storing blood thus entails damaging the red blood corpuscles, which is expressed as functional impairment (for example oxygen release, life and fluidity of the erythrocytes). This is of great significance to the patients requiring a blood transfusion and entails additional expense for blood donation, blood recovery and storage costs.

Various washing stages and the freeze/thaw process considerably disrupt the ion and water balance and reduce the ATP and 2,3-DPG content. This results in an increase in the rate of haemolysis (Sputtek et al., 1992; Langer et al., 1994) and in the impairment of blood viscoelasticity (Langer et al., 1993). Functional degradation of the erythrocytes and structural damage may be attributed, inter alia, to peroxidation of membrane lipids, which may be measured, for example, by means of malonic dialdehyde (Pfafferot et al., 1982).

SUMMARY OF THE INVENTION

The object of the invention was thus to provide an improved method for the preservation of homologous and autologous erythrocyte concentrates for clinical requirements.

This object was achieved according to the invention by using α-lipoic acid and/or the enantiomers thereof and/or the derivatives thereof as additives in liquid stored erythrocytes for homologous and autologous erythrocyte concentrates or as additives in cryogenically stored erythrocytes for homologous and autologous erythrocyte concentrates. The present invention provides both the addition to liquid stored erythrocytes at $4°$ C. for homologous and autologous erythrocyte concentrates and the use of α-lipoic acid and/or the enantiomers thereof and/or the derivatives thereof as additives in cryogenically stored erythrocytes for homologous and autologous erythrocyte concentrates a) for use at $-70°$ C. to $-90°$ C. (glycerol method) and b) in liquid nitrogen $-196°$ C./$-140°$ C. (gas phase, HES method).

An advantageous development of the invention moreover provides the use of D,L-α-lipoic acid and/or the enantiomers thereof and/or the derivatives thereof as additives in cryogenically stored erythrocytes for homologous and autologous erythrocyte concentrates, which were treated with hydroxyethyl starch (HES) and, once thawed, are subsequently further processed with a Cell-(Blood)-Saver.

By means of this additional process, cell detritus (including free haemoglobin) is removed and high quality erythrocyte concentrates obtained. This advantageous version may be used with both the glycerol and the HES method (see above).

According to the invention, the preferred concentration in the blood bag is 10 μM to 1 mM, particularly preferably 100 μM, of D,L-α-lipoic acid and/or the enantiomers thereof and/or the derivatives thereof.

For the purposes of the invention, derivatives are considered to be dihydrolipoic acid, metabolites such as (6,8-bisnortetralipoic acid; tetranorlipoic acid) and the salts and esters and amides of D,L-α-lipoic acid. The process according to the invention for the production of the erythrocyte concentrates used using the stabilisers CPDA-1 and SAG-M is represented schematically in FIG. 1.

The process according to the invention exhibits the following essential features or advantages:

1. Improvement of erythrocyte functionality by means of improved viscoelasticity and increased 2,3-DPG content
2. Increase of erythrocyte life in storage
3. Extension of storage times
4. Restoration of normal erythrocyte function.

The above-stated advantages of the invention are achieved by the addition of α-lipoic acid and/or the enantiomers thereof and/or the derivatives thereof before storage of the liquid stored erythrocytes (at $4°$ C.) for homologous and autologous erythrocytes and in cryogenically stored erythrocytes for use at −70° C. to −90° C. and in liquid nitrogen −196° C./−140° C. (gas phase) for homologous and autologous erythrocyte concentrates.

On the one hand, the above-stated advantage is achieved by the addition according to the invention of α-lipoic acid and/or the enantiomers thereof and/or the derivatives thereof before storage of the stored blood and, on the other hand, in addition to the described process, novelty resides in the use of the above-stated substances. According to the invention, the term derivatives in particular includes dihydrolipoic acid, metabolites (6,8-bisnortetralipoic acid; tetralipoic acid) and the salts of α-lipoic acid together with the esters and amides thereof.

BRIEF DESCRIPTION OF THE DRAWING

FIG. 1. Process for the production of the erythrocyte concentrates using stabilisers CPDA-1 and SAG-M

DETAILED DESCRIPTION OF THE INVENTION

Method

The results obtained here were achieved with human erythrocytes by using the prior art processes for blood and blood bags described above.

In order to establish the effectiveness of D,L-α-lipoic acid and/or the enantiomers thereof and/or the derivatives thereof, the specific method of sinusoidal, oscillating capillary rheometry (Chmiel H., 1990) was used in addition to biochemical test methods. Measurement of the viscoelastic flow properties of blood is used as the most modern method of determining pathological changes in erythrocytes in clinical haemorheology (for example in arterial occlusion, stroke and generally in peripheral circulatory disorders).

In order to determine viscoelasticity, dynamic rheological tests are performed in which deformation and shear stress are measured as a function of time (sinusoidal oscillating shear tests). As a non-linear viscoelastic fluid, blood exhibits a decrease in $\eta'$ and $\eta''$ as shear amplitude increases.

The measurements shown here in the "Examples" were made using the OCR-D oscillating capillary rheometer (A. Paar, Graz, Austria), in which the method is based upon simultaneously determining the volume flow rate and pressure gradient along a glass capillary with a round cross-section. Viscoelasticity may thus distinguish between elastic (energy-storing) and viscous (energy-consuming) deformation. Increasing values of $\eta''$ denote greater aggregation and more rigid cells with the formation of increasingly more elastic erythrocytes (less flexible) with the formation of aggregates, which result in disruption to microcirculatory blood flow. These properties are associated with the structure of the cell membrane and the "bridging" mechanism which give rise to the above-stated rouleau formation. The decrease in $\eta'$ at higher shear rates may result from changes in orientation and elongation of the erythrocytes and from a reduction in energy consumption. $\eta'$ is dependent not only upon the haematocrit and plasma viscosity, but also upon the aggregation behaviour and elastic properties of the membrane.

The action of the substances used in this case has the following effects in stored blood:

A. Erythrocyte concentrates

1. The increase in blood viscosity (dynamic component $\eta'$) caused by ageing was virtually completely suppressed, while the control blood became increasingly viscous with longer storage times. The viscosity of the above-stated substances remained fixed at the value prevailing after 15 days (the difference relative to the control may be 10% or more, corresponding to 100% compensation of the ageing-determined degradation).
2. The elastic component of blood viscosity ($\eta''$) describes the elastic properties of the blood cells. As the stored blood increases in age, the elastic component of blood viscosity increases, thereby resulting in an increase in total viscosity. The differences relative to the control were 20% for this parameter and the age-determined degradation of cell fluidity was completely offset. The cell-bound action of α-lipoic acid is of significance here.
3. Increase of 2,3-DPG (diphosphoglycerate) by 50% after 50 days.
4. The elevated compatibility of the α-lipoic acid used here has been proven over some decades of medicinal use in other applications. Other substances providing protection against oxidative stress under storage conditions are less effective and associated with side effects for patients after blood transfusion (Knight J. A., et al., 1992). The already known anti-oxidative effect of α-lipoic acid resulted in all forms in an approximately 20% reduction in malonic dialdehyde (halving of damage).

B. Cryogenically stored products

1. The values for erythrocyte aggregability in the control group after thawing and resuspension corresponded to those after 15 days of liquid storage. Significantly higher values (by 33%), i.e. approaching the normal range, were achieved by adding our above-stated substances. The action on malonic dialdehyde and viscoelasticity is the same as in A.

Advantages of the novel development

Changes in cellular structures and structure-related functions (blood viscosity and cell fluidity) determined by storage or ageing may be reduced or completely avoided. The effect is even more pronounced if the above-stated substances are used as soon as possible (before storage) and thus before damage has occurred (priming).

It has furthermore been found that the action of such priming effects also continues during resuspension and incubation in autologous plasma (=simulation of retransfusion).

The above-stated substances retain their activity over extended periods of storage (60 days) and even after a freeze/thaw process.

Increase in 2,3-DPG, improved viscoelasticity, non-toxic as additive.

The possibility of storing blood for longer improves the provision of supplies to the population because according to the prior art stored blood must be disposed of after approximately 35 days (limited quantity of donated blood). This thus relieves the pressure upon blood donation services and the supply of their associated hospitals with blood is improved (cost reduction).

The physiological compatibility of α-lipoic acid.

EXAMPLES

Case 1: Erythrocyte concentrates (see prior art)

Case 2: Cryogenically stored erythrocytes (see prior art)

Citations to references contained herein are listed below for convenience and are hereby incorporated by reference.

Chmiel, H. et al. (1990) Biorheology 27:883–94.

Langer et al. (1994) Infusionsther Transfusionsmed 21:393–400.

Pfafferot et al. (1982) Blood 59:12–15.

Sputtek et al. (1992) Infusionsther Transfusionsmed 19:269–275.

Sputtek & Körber (1991) in: Fuller, B. J. and Grout B. W. W., 1991 Clinical Applications of Crybiology. CRC Press.

Stangel, W. et al. (1988) Beitr. Infusionther. 21:103–8, 21:109–12, 21: 127–9.

What is claimed is:

1. A method of storing erythrocytes wherein the erythrocytes have improved viscoelasticity, increased 2,3-diphosphoglycerate content, increased erythrocyte viability or increased storage life compared to untreated erythrocytes comprising treating erythrocytes by adding D,L-α-lipoic acid or one enantiomer thereof or dihydrolipoic acid or 6,8-bisnortetralipoic acid or tetranorlipoic acid in a concentration of about 10 μM to 1 mM to erythrocytes, and storing the erythrocytes.

2. The method of claim 1, wherein the concentration of D,L-α-lipoic acid or enantiomer thereof or dihydrolipoic acid or 6,8-bisnortetralipoic acid or tetranorlipoic acid is about 100 μM.

3. The method of claim 1 wherein the storage is at 4° C.

4. The method of claim 1, further comprising adding glycerol to the erythrocytes in a concentration sufficient to cryoprotect the erythrocytes, wherein the storage is at −70° to −90° C.

5. The method of claim 1, further comprising adding hydroxyethylstarch to the erythrocytes in a concentration sufficient to cryoprotect the erythrocytes, wherein the storage is at −140° to −196° C.

6. A process for the production of erythrocyte concentrates comprising adding a solution comprising citric acid, phosphate and adenine to whole blood; producing an erythrocyte concentrate; and adding a solution comprising saline, adenine, glucose and mannitol, and at least one of D,L-α-lipoic acid, an enantiomer thereof or dihydrolipoic acid, 6,8-bisnortetralipoic acid or tetranorlipoic acid in a concentration of about 10 μM to 1 mM in accordance with FIG. 1.

* * * * *